(12) United States Patent
Fujiwara

(10) Patent No.: US 8,803,070 B2
(45) Date of Patent: Aug. 12, 2014

(54) BIOLOGICAL OPTICAL MEASUREMENT INSTRUMENT AND METHOD FOR DETERMINING DAMAGE OF OPTICAL FIBERS

(75) Inventor: Michiyuki Fujiwara, Tokyo (JP)

(73) Assignee: Hitachi Medical Corporation, Tokyo (JP)

(*) Notice: Subject to any disclaimer, the term of this patent is extended or adjusted under 35 U.S.C. 154(b) by 336 days.

(21) Appl. No.: 13/263,036

(22) PCT Filed: Apr. 5, 2010

(86) PCT No.: PCT/JP2010/056150
§ 371 (c)(1),
(2), (4) Date: Oct. 5, 2011

(87) PCT Pub. No.: WO2010/116964
PCT Pub. Date: Oct. 14, 2010

(65) Prior Publication Data
US 2012/0033201 A1    Feb. 9, 2012

(30) Foreign Application Priority Data

Apr. 8, 2009  (JP) ................................. 2009-093488

(51) Int. Cl.
| | | |
|---|---|---|
| *G01J 1/04* | (2006.01) | |
| *A61B 5/145* | (2006.01) | |
| *A61B 5/1455* | (2006.01) | |
| *A61B 5/05* | (2006.01) | |
| *G01M 11/08* | (2006.01) | |
| *A61B 5/1495* | (2006.01) | |
| *G02B 6/10* | (2006.01) | |
| *G01N 21/35* | (2014.01) | |

(52) U.S. Cl.
CPC ............. *A61B 5/1495* (2013.01); *A61B 5/1455* (2013.01); *G02B 6/102* (2013.01); *A61B 2562/228* (2013.01); *A61B 2560/0276* (2013.01); *A61B 5/05* (2013.01); *G01N 21/359* (2013.01); *A61B 2560/0233* (2013.01); *G01M 11/08* (2013.01); *A61B 2562/223* (2013.01)
USPC ................ 250/227.11; 250/338.1; 356/239.2; 356/237.1; 398/20

(58) Field of Classification Search
CPC ....... G01N 21/00; G01N 21/359; G01B 1/16; G01M 5/0033; G01M 5/0091; G01M 11/0088; A61B 18/22; A61B 5/1455; A61B 5/1495; A61B 5/05; A61B 2562/223; A61B 2562/228; A61B 2560/0233; A61B 2560/0276; G02B 6/00; G02B 6/102
USPC .......... 356/237.1, 239.1, 239.2, 73.1; 398/20, 398/21, 200; 250/227.11, 573, 574, 338.1; 385/147, 31, 14
See application file for complete search history.

(56) References Cited

U.S. PATENT DOCUMENTS

| | | | |
|---|---|---|---|
| 6,069,691 A | 5/2000 | Rosow et al. | |
| 6,885,801 B1 | 4/2005 | Shankar et al. | |
| 7,428,354 B2 * | 9/2008 | Miyazaki ........................ | 385/24 |
| 7,536,102 B1 * | 5/2009 | Huffman et al. ................ | 398/21 |
| 2006/0178839 A1 | 8/2006 | Maki et al. | |
| 2008/0285017 A1 | 11/2008 | Mitchell et al. | |
| 2009/0028550 A1 | 1/2009 | Zhang et al. | |
| 2009/0054885 A1 * | 2/2009 | Kawasaki et al. ............... | 606/16 |
| 2011/0013905 A1 * | 1/2011 | Wang et al. ..................... | 398/21 |

FOREIGN PATENT DOCUMENTS

| | | | |
|---|---|---|---|
| JP | 2001137247 A | | 5/2001 |
| JP | 2002-323444 | | 11/2002 |
| JP | 2007-209680 | * | 8/2007 |
| JP | 2007209680 A | | 8/2007 |
| JP | 2008-86407 | | 4/2008 |
| JP | 2009-22353 | | 2/2009 |

OTHER PUBLICATIONS

Machine Translation JP 2007-209680.*
International Search Report for PCT International Application No. PCT/JP2010/056150, mailed Jul. 13, 2010.

* cited by examiner

Primary Examiner — David Porta
Assistant Examiner — Yara B Green
(74) Attorney, Agent, or Firm — Brundidge & Stanger, P.C.

(57) ABSTRACT

A biological optical measurement instrument has a gain adjustment unit (40) configured to set the gain value according to the intensity of the passing light in the measurement data detected by the optical measurement unit (12), a gain storage unit (44) configured to store the damage gain value set by the gain adjustment unit (40) when a damaged incident optical fiber (6*a*) or a damaged detection optical fiber (8*a*) is used, a gain comparison unit (42) configured to compare the gain value set by the gain adjustment unit (40) and the damage gain value stored in the gain storage unit (44), and a damage determination unit (46) configured to determine whether or not the incident optical fiber (6*a*) or the detection optical fiber (8*a*) is damaged on the basis of the comparison result by the gain comparison unit (42).

The display unit (36) displays the damage condition.

13 Claims, 7 Drawing Sheets

BIOLOGICAL OPTICAL MEASUREMENT INSTRUMENT AND METHOD FOR DETERMINING DAMAGE OF OPTICAL FIBERS

FIELD OF THE INVENTION

The present invention relates to a biological optical measurement instrument which irradiates a near-infrared light to an object and measures the light passed through the object or reflected inside of the object so as to measure blood circulation, hemodynamic status and variation of hemoglobin, and the method for determining damage of optical fibers.

DESCRIPTION OF RELATED ART

A biological optical measurement instrument is capable of harmlessly measuring blood circulation, hemodynamic status and hemoglobin variation in an object without putting the object under much restriction. In recent years, imaging of measurement data using a multi-channel device has been developed, and its clinical application has been expected.

The biological optical measurement instrument in Patent Document 1 discloses the technique for displaying on a display unit the incident position or detection position corresponding to the measurement position without enough light intensity detected from a light measurement unit using a different display method from that of displaying the incident position and detection position corresponding to the measurement position with acceptable light intensity (for example, Patent Document 1).

PRIOR ART DOCUMENTS

Patent Document 1: JP-A-2008-86407

In the biological optical measurement instrument disclosed in Patent Document 1 determines a damaged part of optical fibers by whether or not the light intensity detected from the light measurement unit falls short or not in the condition that a probe is applied to the object. However, it is assumed that whether the source of failure is attributed to damage of optical fibers or not cannot be determined by merely referring to shortage of light intensity in the condition that a probe is applied to the object.

The objective of the present invention is to provide a biological optical measurement instrument and method for determining damage of optical fibers capable of accurately recognizing the damaged condition of optical fibers.

BRIEF SUMMARY OF THE INVENTION

In order to achieve the above-described objective, the biological optical measurement instrument of the present invention comprising:
- a light source unit including an incident optical fiber that irradiates a near-infrared light;
- a photometry unit including a detection optical fiber that measures a passing light at a plurality of measurement points in an object;
- a signal processing unit configured to process the measurement data outputted from the photometry unit and thereby generating an image thereof; and
- a display unit configured to display the measurement data in the signal processing unit, is characterized in further comprising:
- a gain adjustment unit configured to set a gain value on the measurement data detected by the photometry unit based on the light intensity of the passing light;
- a gain storage unit configured to store a damage gain value set by the gain adjustment unit when a damaged incident optical fiber or a damaged detection optical fiber is used;
- a gain comparison unit configured to compare the gain value set in the gain adjustment unit and the damage gain value stored in the gain storage unit; and
- a damage determination unit configured to determine whether or not the incident optical fiber or the detection optical fiber is damaged or not based on the comparison result in the gain comparison unit,
- wherein the display unit displays the determined damage condition. Accordingly, an operator can determine which optical fiber is damaged.

Also, the method for determining damage of optical fibers includes:
- a step of setting a gain value on the measurement data detected by a photometry unit based on the light intensity of a passing light;
- a step of storing the set damage gain value when a damaged incident optical fiber or a damaged detection optical fiber is used;
- a step of comparing the gain value and the damage gain value; and
- a step of determining whether or not the incident optical fiber or the detection optical fiber is damaged based on the comparison result between the gain value and the damage gain value.

Effect of the Invention

In accordance with the present invention, it is possible to accurately grasp the damage condition of optical fibers.

DETAILED DESCRIPTION OF THE INVENTION

Preferable embodiments of the present invention will be described below referring to the attached diagrams.

Embodiment 1

Figure 1:
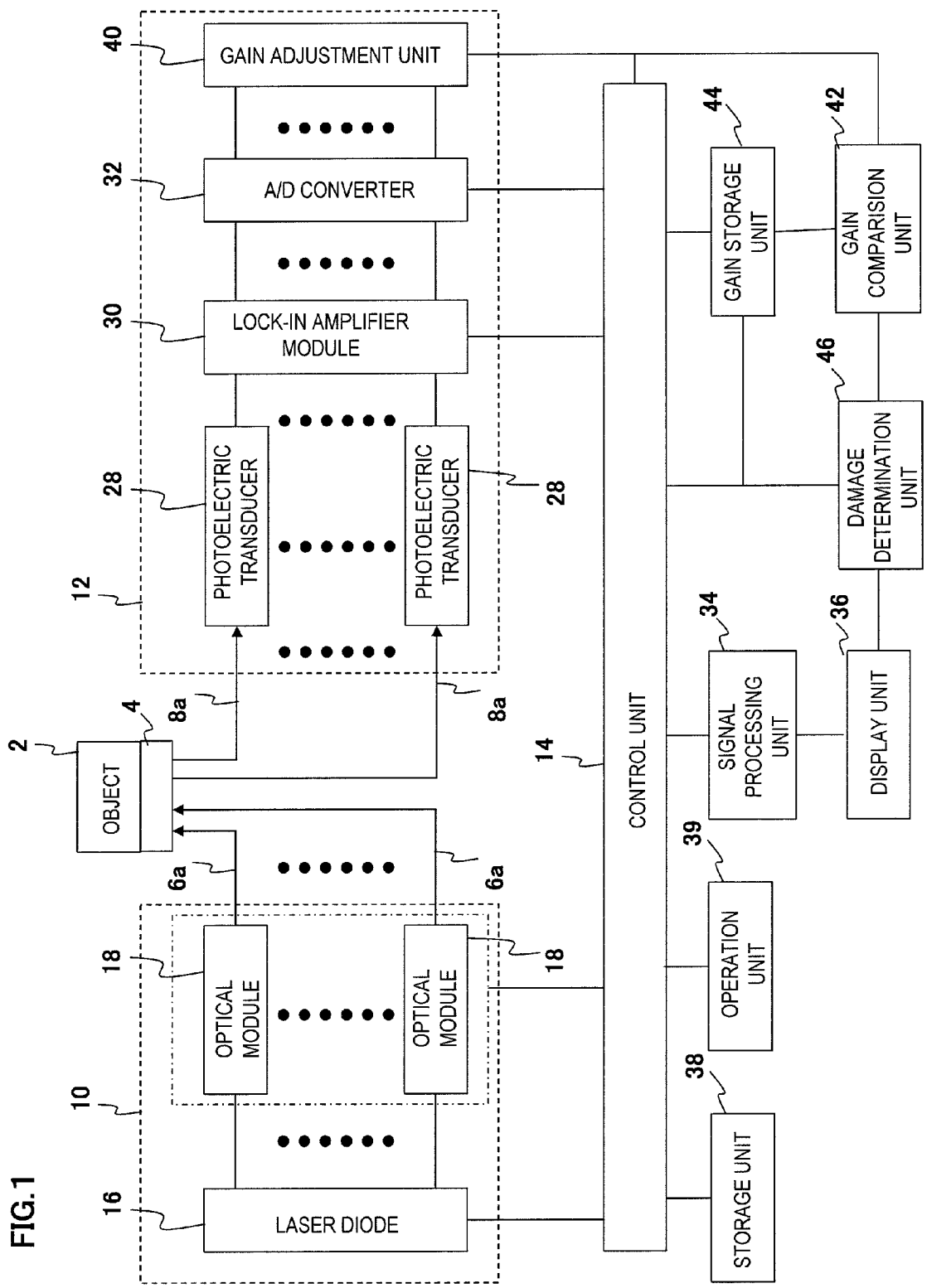
FIG. 1 is a block diagram showing a biological optical measurement instrument of the present invention.

FIG. 1 is a block diagram showing a biological optical measurement instrument of the present invention. In FIG. 1, a probe holder 4 is applied to a head region of an object to be examined. The near-infrared light generated in an optical source unit 10 is irradiated to an object 2 via a plurality of incident optical fibers 6a. The apical portions of the respective incident optical fibers 6a are applied to the probe holder 4 via incident probes 6.

The light source 10 has a laser diode 16 that irradiates a light having a predetermined wavelength and a plurality of optical modules 18 that modulate the light from the laser diode 16. The respective optical modules 18 have a modulator (not shown in the diagram) which modulates the light from the laser diode 16 with respectively different frequencies. The wavelength of a light depends on the spectral characteristics of a target component in a body. In the case of measuring oxygen saturation or amount of blood from density of Hb and Hb02, one or more wavelengths are selected to be used from among the wavelength range of 600 nm~1400 nm.

The light which is irradiated to the object 2 from the incident optical fibers 6a and passed through the object 2 is transmitted to an optical measurement unit 12 via a plurality of detection optical fibers 8a. The apical portions of the respective detection optical fibers 8a are applied to the probe holder 4 via the detection probes 8. The probe holder 4 contains a plurality of incident probes 6 and a plurality of detection probes 8. The incident probes 6 and the detection probes 8 are alternately disposed in a matrix pattern.

The optical measurement unit 12 has a plurality of photoelectric transducers 28 such as photo diode which generates an electric signal according to the light intensity of the detected passing light, a lock-in amplifier module 30 which selectively detects the module signal corresponding to an electric signal from the photoelectric transducers 28, an A/D converter 32 which converts the output signal from the lock-in amplifier module 30 into digital measurement data, and a gain adjustment unit 40 which multiplies measurement data by the gain value based on the light intensity of the detected passing light.

For example, in the case of measuring two kinds of oxygenated hemoglobin and deoxygenated hemoglobin, the lights having two kinds of wavelength that are 780 nm and 830 nm are generated, and these lights are synthesized to be irradiated to the object 2 from one incident optical fiber 6a. Then the modulating signal corresponding to these two wavelengths is selectively detected by the lock-in amplifier module 30. In this manner, twice the number of channels of hemoglobin content variation signals can be acquired with respect to the measurement position between the optical incident position from the incident optical fiber 6a and the detection position of the passing light by the detection optical fiber 8a.

The gain adjustment unit 40 multiplies the measurement data outputted from the A/D converter 32 by a gain value on the basis of the electrical signal based on the light intensity of the passing light detected by a plurality of photoelectric transducers 28.

A control unit 14 is configured by, for example a computer. A signal processing unit 34 processes a hemoglobin content variation signal and creates the measurement data for plotting the graph which shows change of oxygenated hemoglobin concentration, deoxygenated hemoglobin concentration, total-hemoglobin concentration, etc. for every channel on a 2-dimensional image of the object 2. Also, a storage unit 38 records the measurement data necessary for the processing by the signal processing unit 34 or analysis result of the measurement data. Various commands necessary for operation of the control unit 14 are inputted to an operation unit 39. A display unit 36 which displays the measurement data created by the signal processing unit 34 or analysis result of the measurement data is connected to the signal processing unit 34. The display unit 36 displays the measurement data created in the signal processing unit 34.

The control unit 14 further comprises a storage unit 44 configured to store the damage gain value set in the gain adjustment unit 40 when a damaged incident optical fiber 6a or a damaged detection optical fiber 8a is used, a gain comparison unit 42 configured to compare the gain value set by the gain adjustment unit 40 on the measurement data to be used for an actual measurement acquired using the incident optical fiber 6a and the detection optical fiber 8a with the damaged gain value stored in the storage unit 44, and a damage determination unit 46 configured to determine whether an incident optical fiber 6a or a detection optical fiber 8a is damaged or not based on the comparison result acquired in the gain comparison unit. The damage condition determined by the damage determination unit 46 is then displayed on the display unit 36. The respective components such as the light source unit 10 or the optical measurement unit 12 are controlled by the control unit 14.

Figure 2:
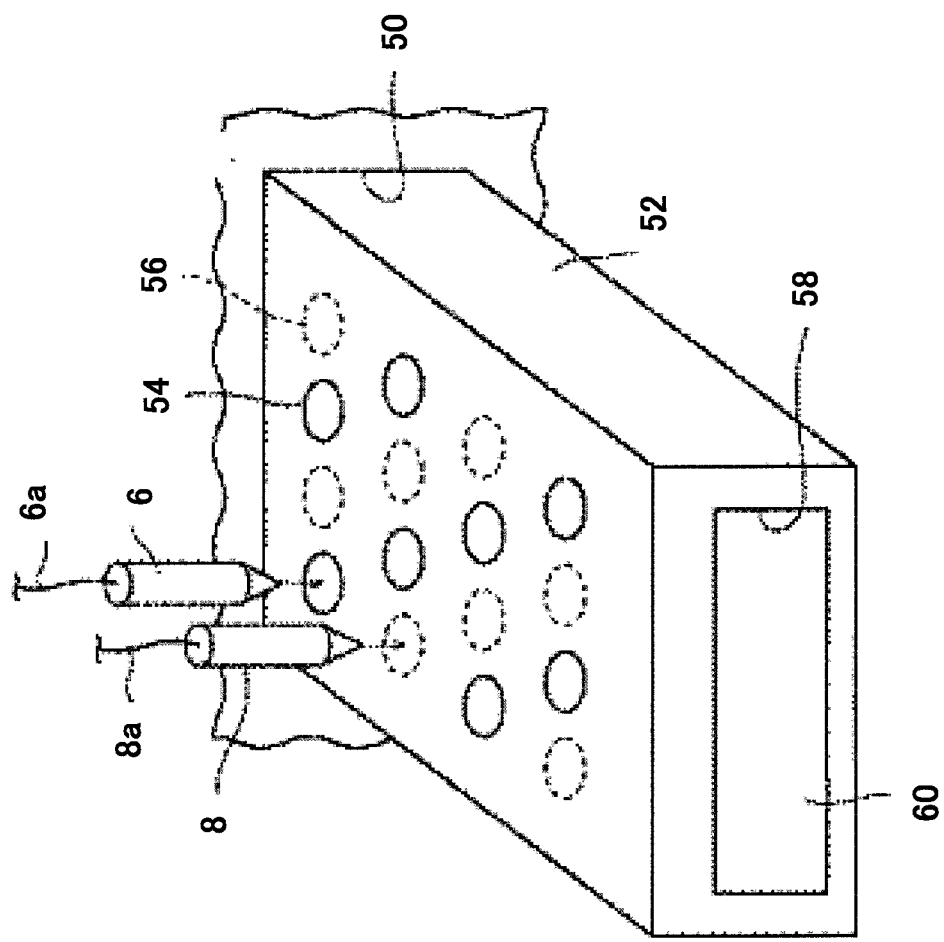
FIG. 2 is a perspective view of an inspection unit of the biological optical measurement instrument related to the present invention.

FIG. 2 is a perspective view showing an inspection unit for a biological optical measurement instrument. The biological optical measurement instrument is provided with the inspection unit which inspects incident optical fibers 6a or detection optical fibers 8a. A holder insert-hole 50 is provided on the wall surface of a main body of the biological optical measurement instrument. A base end section of a tabular inspection-unit holder 52 is inserted into the holder insert-hole 50. The inspection-unit holder 52 is pulled out from the main body upon inspection as shown in FIG. 2, and pressed into the main body to be stored when inspection is not being carried out. In other words, the inspection-unit holder 52 can be slid in and out horizontally between the inspecting position and the stored position.

On the upper part of the inspection-unit holder 52, a plurality of incident-probe application parts (mounting holes) and a plurality of detection-probe application parts (mounting holes) 56 are provided. In FIG. 2, the incident-probe application parts 54 are indicated by solid lines and the detection-probe application parts 56 are indicated by dashed lines. The incident-probe application parts 54 and the detection-probe application parts 56 are disposed in a matrix pattern at predetermined intervals (for example, 30 mm).

To the respective incident-probe application parts 54, the incident probes 6 for irradiating a light are applied (inserted). The detection probes 8 for receiving the passed light are applied (inserted) to the respective detection-probe application parts 56.

Inside of the inspection-unit holder 52, an inspection unit insert-hole 58 is provided as an inspection unit application unit giving on to the incident-probe application parts 54 and the detection-probe application parts 56. The incident-probe application parts 54 and the detection-probe application parts 56 are communicated with the inspection unit insert-hole 58. Also, the inspection unit insert-hole 58 is opened at the frontal surface of the inspection-unit holder 52.

Into the inspection unit insert-hole 58, plural kinds of inspection units that output different information for implementing inspections related to the incident state and optical reception state by receiving lights from the incident probes 6 inserted into the incident-probe application parts 54 are selectively inserted. In this example, a light-detection inspection unit 60 or a light-intensity inspection unit 60 is inserted into the inspection unit insert-hole 58 as an inspection unit.

Figure 3:
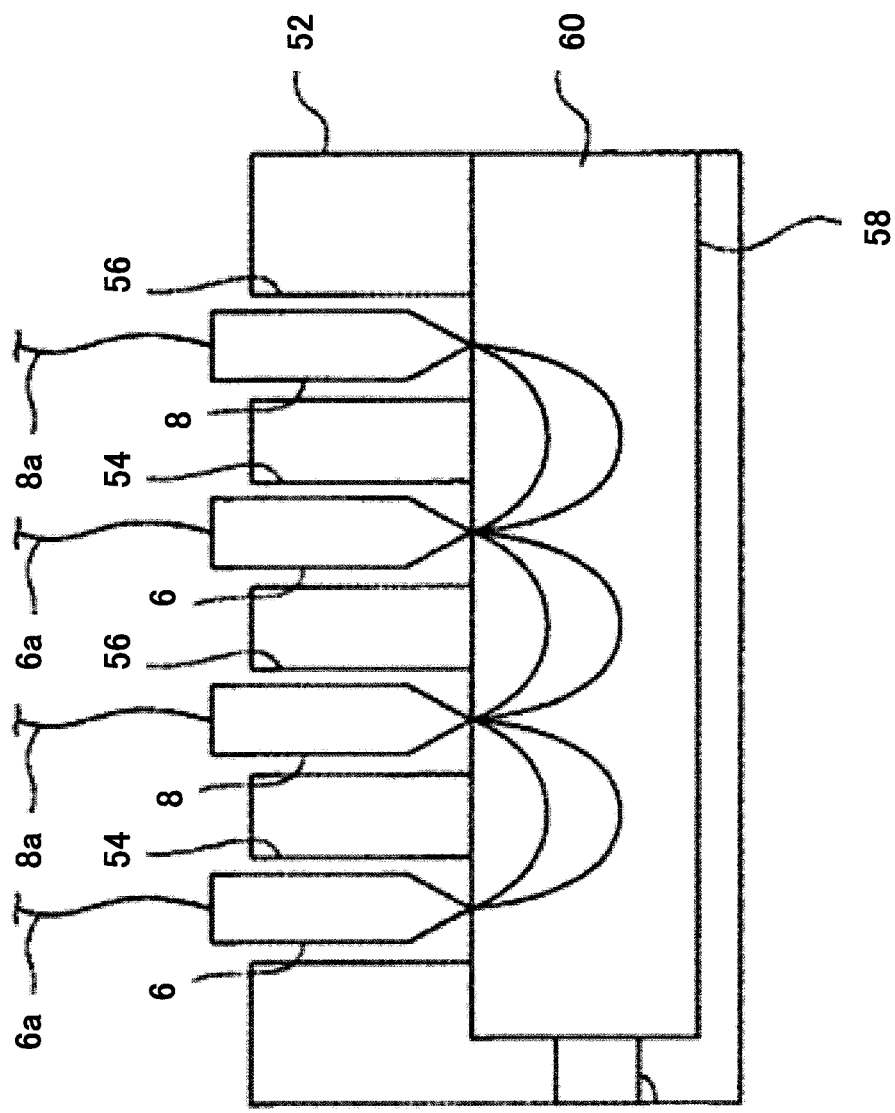
FIG. 3 is a cross-sectional view showing the inspection unit of the biological optical measurement instrument related to the present invention.

FIG. 3 is a cross-sectional view showing an inspection unit of a biological optical measurement instrument, and illustrates the state that the light-detection inspection unit 60 is inserted into the inspection unit insert-hole 58 in FIG. 2. The light-detection inspection unit 60 attenuates and passes the light from the incident probe 6, and causes the detection probes 8 to receive the passed light (information for carrying out the inspection). More specifically, the light-detection inspection unit 60 is formed by a tabular light scatterer and functions as a biological simulated sample (phantom). Operation of the entire biological optical measurement instrument can be inspected by measuring the light passed through the light-detection inspection unit 60 and received by the detection probes 8.

The first embodiment is to be executed in the condition that an inspection unit of a biological optical measurement instrument is being used while the incident probes 6 are applied (inserted) into the respective incident-probe application parts 54 and the detection probes 8 are applied (inserted) into the respective detection-probe application parts 56.

When the light which is irradiated from the incident probes 6 (incident optical fibers 6a), passes through the light-detection inspection unit 60 and received by the detection probes 8 (detection optical fibers 8a) is measured, the storage unit 44 stores in advance the damage gain value set in the gain adjustment unit 40 using a damaged incident optical fiber 6a or a damaged detection optical fiber 8a. Also, when the light which is irradiated from the incident probes 6 (incident optical fibers 6a), passed through the light-detection inspection unit 60 and received by the detection probes 8 (detection optical fibers 8a) is measured, the gain comparison unit 42 compares the gain value set by the gain adjustment unit 40 with the damaged gain value stored in the storage unit 44. Then the damage determination unit 46 determines whether the incident optical fibers 6a or the detection optical fibers 8a are damaged or not by the comparison result of the gain comparison unit.

The gain value of the gain adjustment unit 40 set upon measuring the light irradiated from the incident probes 6, passed through the light-detection inspection unit 60 and received by the detection probes 8 is the gain specified for uniformizing the detection light intensity. The gain value is for improving the S/N ratio so as to ensure credibility of the measured value.

In concrete terms, the gain adjustment unit 40 multiplies the measurement data by the gain value so that the detection light intensity of the plurality of photoelectric transducers 28 can be uniformized at 2 mW. When the detection light intensity is small (for example, 2 mW or smaller) the gain value to be multiplied by the measurement data becomes great (for example, 1 or greater), and when the detection light intensity is great (for example, 2 mW or greater) the gain value to be multiplied by the measurement data will be small (for example, 1 or smaller).

The storage unit 44 stores the damage gain value set by the gain adjustment unit 40 using a damaged incident optical fiber 6a or a damaged detection optical fiber 8a. The damage gain value is the gain value to be set by the gain adjustment unit 40 in the state that the incident optical fiber 6a or the detection optical fiber 8a is damaged.

For example, when the condition that normal optical fibers of an incident optical fiber 6a or a detection optical fiber 8a is 80% or less, i.e. 20% of the optical fibers is damaged is determined as defect, the control unit 14 obtains in advance the damage gain value using the damaged incident optical fiber 6a or the damaged detection optical fiber 8a in which 20% of the optical fibers are damaged.

In concrete terms, in order to confirm the number of damaged (defect) optical fibers, the number of optical fibers is counted using a stationary-type microscope and a jacklight or a microscope though not shown in the diagram. When a stationary-type microscope and a jacklight are used, an inspection light is irradiated to one end-face of an optical fiber by the jacklight, and the other end-face of the optical fiber is zoomed (about 200 times) and imaged by the microscope so as to count the number of damaged optical fibers in the image. When a microscope is used, the end face of the optical fiber is imaged via the microscope, and the number of damaged optical fibers is counted from the image.

In the imaging of an end face of an optical fiber, the binarization process is executed on the luminance (hue information) of individual pixels. The binarization process converts the luminance of each pixel into two values of black and white using a determinate reference value. The black color is a damaged optical fiber, and the white color is an optical fiber which is not damaged.

The number of pixels in the entire image is set as 100%, and the control unit 14 calculates the ratio of black pixels among the pixels of the entire image. When the ratio of the number of black pixels among the number of pixels in the entire image is calculated as 10%, it means that 10% of the incident optical fiber 6a or the detection optical fiber 8a is damaged. Also, when the ratio of black pixels among the pixels of the entire image is calculated as 20%, it means that 20% of the incident optical fiber 6a or the detection optical fiber 8a is damaged.

Then an operator prepares the incident optical fibers 6a or the detection optical fibers 8a of which the 20% of optical fibers are damaged based on the image as described above. Then the control unit 14 calculates the gain value set by the gain adjustment unit 40 using the incident optical fibers 6a or the detection optical fibers 8a of which the 20% of optical fibers are damaged. The control unit 14 causes the gain storage unit 44 to store the calculated gain value.

Then the gain comparison unit 42 compares the gain value set by the gain adjustment unit 40 on the measurement data which is acquired using the incident optical fiber 6a and the detection optical fiber 8a to be used in an actual measurement with the damaged gain value stored in the storage unit 44. In concrete terms, the damage determination unit 46 determines whether the gain value of the optical fiber to be used for an actual measurement is higher or lower than the damage gain value.

Figure 4:
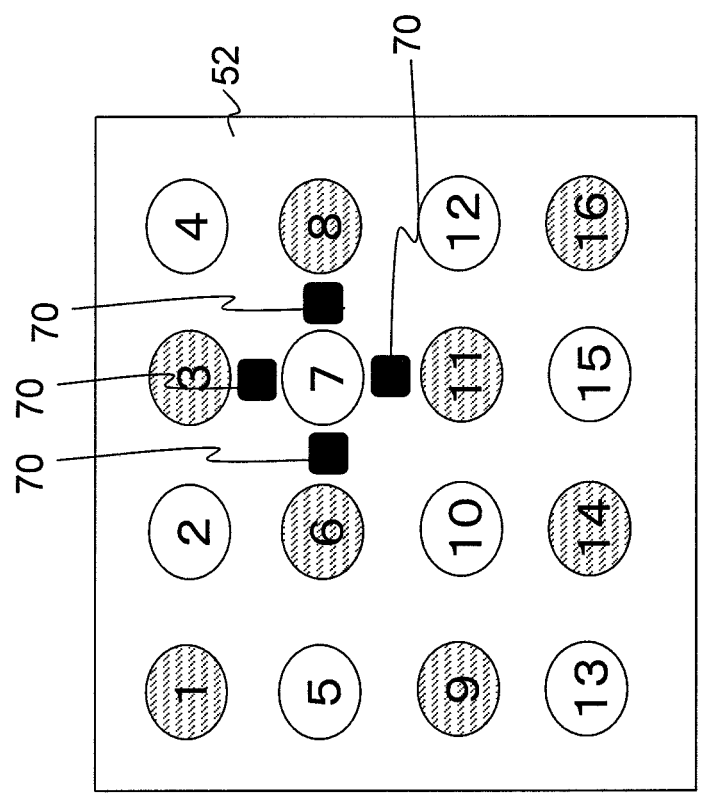
FIG. 4 is a display of damage information and positional information on a damaged optical fiber related to the present invention.

When the gain value to be multiplied by the measurement data acquired using the incident optical fiber 6a and the detection optical fiber 8a to be used for an actual measurement is higher than the damage gain value, the damage determination unit 46 determines that the incident optical fibers 6a or the detection optical fibers 8a to be used is damaged (defect). When the gain value to be multiplied by the measurement data acquired using the incident optical fiber 6a and the detection optical fiber 8a to be used in an actual measurement is lower than the damage gain value, damage determination unit 46 determines that the incident optical fiber 6a or the detection optical fiber 8a is not damaged (normal). The display unit 36 displays damage information and positional information of the damaged incident optical fiber 6a or the damaged detection optical fiber 8a as shown in FIG. 4. FIG. 4 is a screen in which damage information and positional information of the incident optical fibers 6a or the detection optical fibers 8a is displayed.

The incident optical fibers 6a are shown in the positions of 1, 3, 6, 8, 9, 11, 14 and 16 in FIG. 4. The detection optical fibers 8a are shown in the positions of 2, 4, 5, 7, 10, 12, 13 and 15. When the damage determination unit 46 determines that the gain value to be multiplied by the measurement data acquired using the incident optical fibers 6a and the detection optical fibers 8a to be used for an actual measurement is higher than the damage gain value, the display unit 36 displays marks 70 at the places where the gain value is higher than the damage gain value.

If the incident optical fiber 6a or the detection optical fiber 8a is damaged, the gain values at four places around the damaged optical fiber become high. Here, the "7" of the detection optical fibers 8a wherein the marks 70 are displayed in four places in the periphery thereof is damaged. The operator can determine which optical fiber is damaged by referring to the number of the incident optical fiber 6a or the detection optical fiber 8a wherein the marks 70 are displayed at four places of the periphery thereof.

In this case, since the damaged incident optical fiber 6a or the damaged detection optical fiber 8a needs to be replaced, the display unit 36 displays the positional information and a warning message on the damaged incident optical fiber 6a or the damaged detection optical fiber 8a. The display unit 36 can also display information such as the replacement method of the damaged incident optical fiber 6a or the detection optical fiber 8a and contact addresses of maintenance companies.

Figure 5:
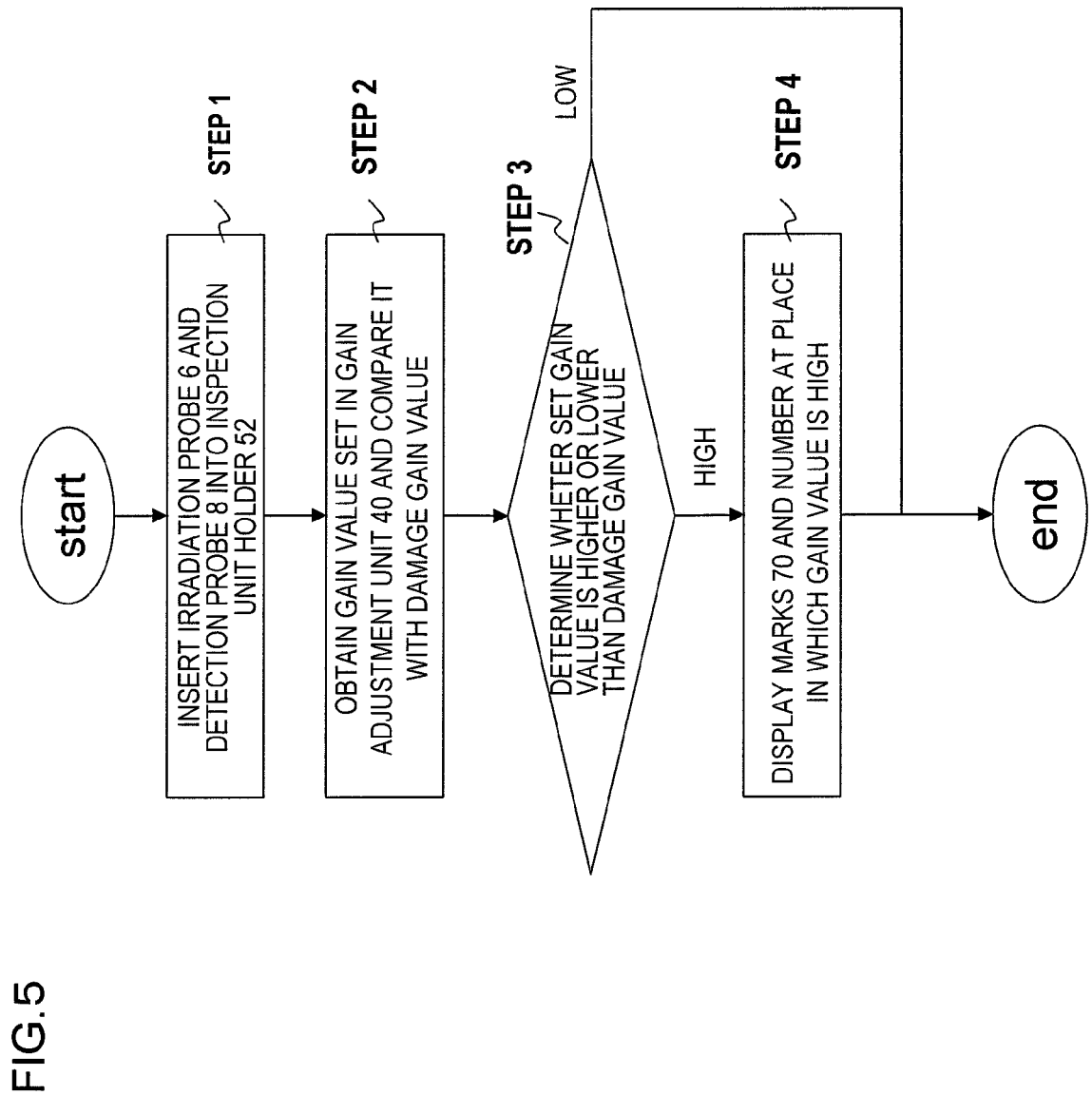
FIG. 5 is a flowchart showing operation of a first embodiment related to the present invention.

Operation in the first embodiment will be described using FIG. 5.
(Step 1)
Into the inspection-unit holder 52 which is formed by a tabular light scatterer and has a light-detection inspection unit 60 that functions as a biological simulated sample (phantom), the incident probe 6 and the detection probe 8 to be used for an actual measurement are inserted.
(Step 2)
The gain comparison unit 42 obtains the gain value set by the gain adjustment unit 40 on the measurement data acquired using the incident optical fiber 6a and the detection optical fiber 8a to be used for an actual measurement, and compares the obtained gain value with the damage gain value previously stored in the gain storage unit 44.
(Step 3)
In the case that the gain value to be multiplied by the measurement data acquired using the incident optical fiber 6a and the detection optical fiber 8a to be used for an actual measurement is higher than the previously acquired damage gain value, the damage determination unit 46 determines that the incident optical fiber 6a or the detection optical fiber 8a to be used for an actual measurement is damaged (defect).
(Step 4)
The display unit 36 displays the positional information and a warning message about the damaged incident optical fiber 6a or the damaged detection optical fiber 8a. In concrete terms, the display unit 36 displays the number of the incident optical fiber 6a or the detection optical fiber 8a wherein the marks 70 are displayed at four places in the periphery thereof.

As described above, in accordance with the present invention, an operator can accurately grasp the damage condition of incident optical fibers 6a or detection optical fibers 8a. The operator can also arbitrarily replace the damaged incident optical fiber 6a or the damaged detection optical fiber 8a.

Embodiment 2

Figure 6:
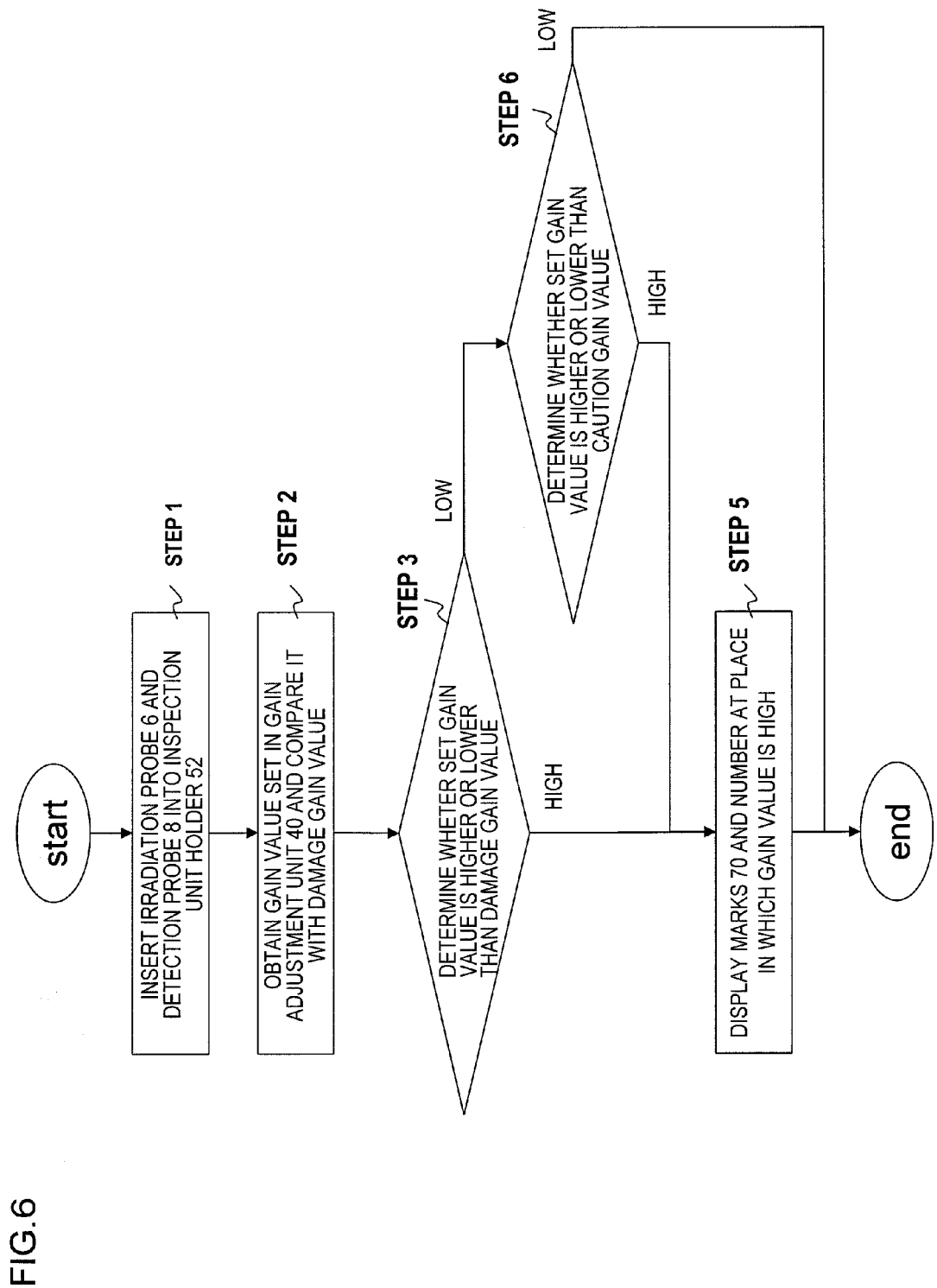
FIG. 6 is a flowchart showing operation of a second embodiment related to the present invention.

Here, the second embodiment will be described referring to FIG. 6. The difference from the first embodiment is that not only damage condition of optical fibers but also almost damaged optical fibers can be acknowledged.

First, as in the first embodiment, an incident optical fiber 6a or a detection optical fiber 8a of which the 20% thereof is damaged and an incident optical fibers 6a or a detection optical fibers 8a of which the 10% thereof is damaged are prepared. Then using the damaged incident optical fiber 6a or the damaged detection optical fiber 8a, i.e. the incident optical fiber 6a or the detection optical fiber 8a wherein the 20% thereof is damaged, the control unit 14 calculates the damage gain value to be set by the gain adjustment unit 40. Also, the control unit 14 calculates a caution gain value to be set by the gain adjustment unit 40 using the almost damaged incident optical fiber 6a or the almost damaged detection optical fiber 8a, i.e. the incident optical fiber 6a or the detection optical fiber 8a wherein the 10% thereof is damaged. The gain storage unit 44 stores the damage gain value and the caution gain value.

Next, operation in the second embodiment will be described using FIG. 6.
(Step 1)
The incident probe 6 and the detection probe 8 to be used in an actual measurement are inserted into the inspection-unit holder 52 formed by a tabular light scatterer and has the light-detecting inspection unit 60 which has a function as a biological simulation sample (phantom).
(Step 2)
The gain comparison unit 42 obtains the gain value set by the gain adjustment unit 40 on the measurement data acquired using the incident optical fiber 6a or the detection optical fiber 8a to be used in an actual measurement, and compares the obtained gain value with the damage gain value and the caution gain value previously stored in the gain storage unit 44.
(Step 3)
In the case that the gain value to be multiplied by the measurement data acquired using the incident optical fiber 6a and the detection optical fiber 8a to be used in an actual measurement is higher than the previously stored damage gain value, the damage determination unit 46 determines that the incident optical fiber 6a or the detection optical fiber 8a to be used for an actual measurement is damaged (defect).
(Step 4)
In the case that the gain value to be multiplied by the measurement data acquired using the incident optical fiber 6a or the detection optical fiber 8a to be used for an actual measurement is higher than the previously stored caution gain value, the damage determination unit 46 determines that the incident optical fiber 6a or the detection optical fiber 8a to be used for an actual measurement is almost damaged.
(Step 5)
The display unit 36 displays the damaged incident optical fiber 6a or the damaged detection optical fiber 8a along with the positional information and a warning message. The display unit 36 displays the almost damaged incident optical fiber 6a or the almost damaged detection optical fiber 8a along with the positional information and a caution message. In concrete terms, the display unit 36 displays the number of the incident optical fiber 6a or the detection optical fiber 8a in which marks 70 are displayed at four places in the periphery thereof.

While a warning message and a caution message are displayed being divided into two levels using a caution gain value and a damage gain value in the second embodiment, the warning or caution message can be divided into three or more levels and displayed.

As described above, in accordance with the present invention, an operator can acknowledge almost damaged incident optical fibers 6a or an almost damaged detection optical fibers 8a before they are damaged, since warning messages and caution messages are called up in plural levels. The operator can also properly replace the damaged or the almost damaged incident optical fiber 6a or the detection optical fiber 8a.

Embodiment 3

The third embodiment will be described below. The difference from the first and second embodiments is that an almost damaged optical fiber can also be acknowledged by tracking record of an optical fiber's damage condition.

Figure 7:
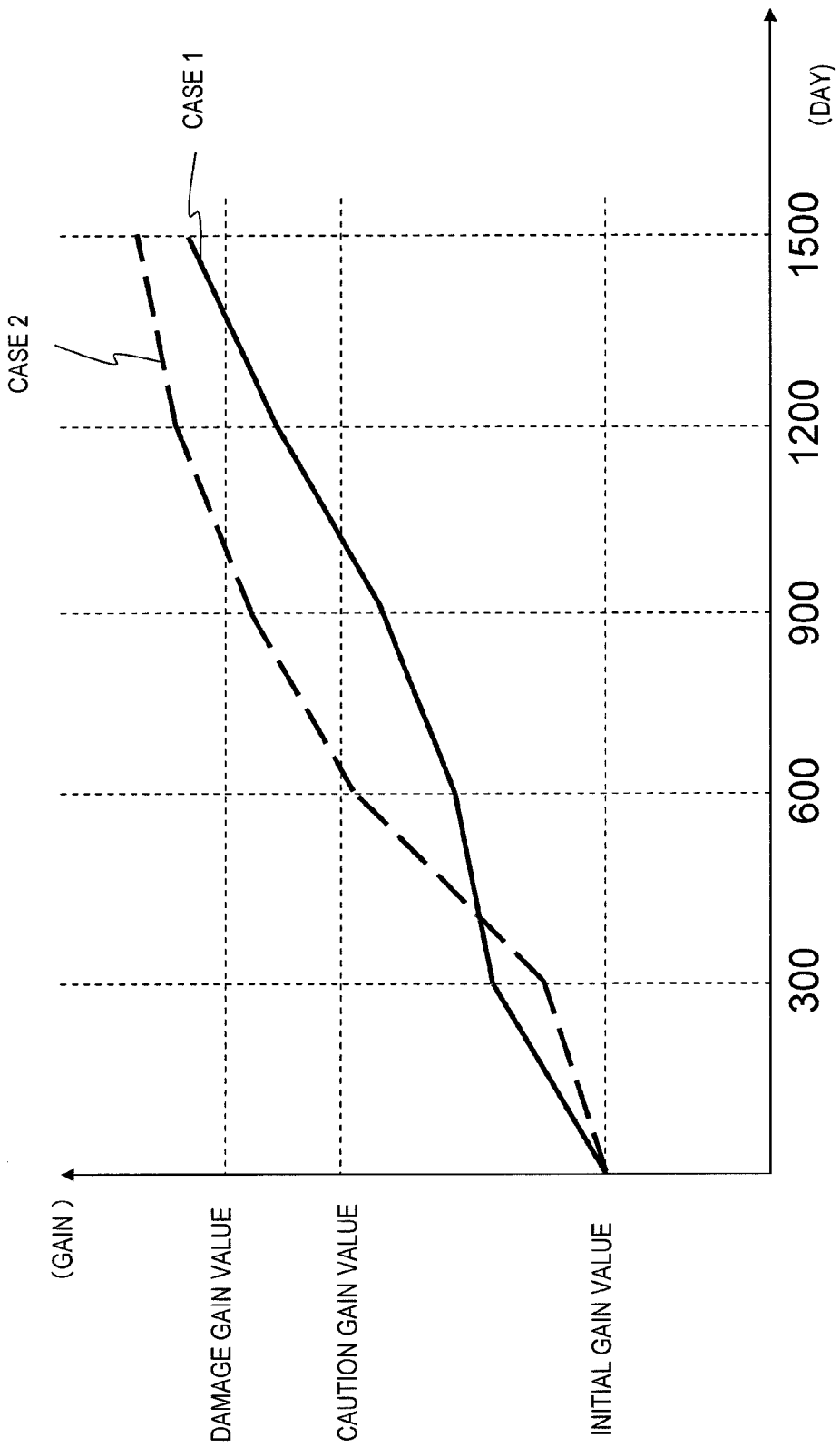
FIG. 7 is a graph for explaining a third embodiment related to the present invention.

FIG. 7 is a graph showing temporal transition of the gain value of a certain incident optical fiber 6a and a detection optical fiber 8a. Case 1 corresponds to temporal degradation and case 2 corresponds to excess strain on the optical fibers.

On the basis of an image showing an end face of an optical fiber, incident optical fibers 6a or detection optical fibers 8a which are not damaged is prepared. The prepared optical fibers are in a brand-new condition.

(Case 1)

After 300 days, 600 days, ... since the delivery date of the optical fibers, the control unit 14 obtains the gain value which is set on the measurement data acquired using the incident optical fiber 6a or the detection optical fiber 8a to be used in an actual measurement. Then the storage unit 44 stores the gain values obtained with time. In this manner, the storage unit 44 stores the gain values obtained with time for the portion of the channels of the incident optical fibers 6a and the detection optical fibers 8a.

In this case, it is assumed that the incident optical fibers 6a and the detection optical fibers 8a are inspected once in every 300 days. The graph shows that the obtained gain value gradually becomes higher. This is due to temporal degradation of the incident optical fibers 6a and the detection optical fibers 8a.

The damage determination unit 46 calculates the day that the gain value surpasses a caution gain value and a damage gain value referring to the transition of the gain value stored in the storage unit. In concrete terms, the damage determination unit 46 calculates the day that the gain value surpasses the caution gain value and the damage gain value before the gain value stored in the storage unit 44 reaches the caution gain value.

First, the damage determination unit 46 calculates the day that the gain value surpasses the caution gain value and the damage gain value on the basis of the relationship between the delivery date of the product with its initial gain value and the date after 300 days from the delivery date with the gain value acquired on that date. The damage determination unit 46 estimates that the gain value will not surpass the caution gain value and the damage gain value in the next inspection (after 600 days) based on the gain value acquired on the first inspection which is 300 days after the delivery of the product and the inclination of the gain value. Thus a warning message or a caution message will not be displayed on the display unit 36 at this time.

Then the damage determination unit 46 estimates that the gain value will not surpass a caution gain value or a damage gain value in the next inspection (after 900 days) based on the gain value acquired on the second inspection which is after 600 days since the delivery date of the product and the inclination of the gain value. Thus a warning message or a caution message will not be displayed on the display unit 36 at this time.

Then the damage determination unit 46 estimates that the gain value will surpass the caution gain value in the next inspection (after 1200 days) based on the gain value acquired on the third inspection which is after 900 days since the delivery date of the product and the inclination of the gain value. And the damage determination unit 46 displays a caution message on the display unit 36.

Then the damage determination unit 46 estimates that the gain value will surpass the damage gain value in the next inspection (after 1500 days) based on the gain value acquired on the fourth inspection which is after 1200 days since the delivery date of the product and the inclination of the gain value. And the damage determination unit 46 displays a warning message on the display unit 36.

As described above, in accordance with the present invention, an operator can estimate the temporal degradation of optical fibers by tracking record of damage condition of the optical fibers, and acknowledge the optical fibers that are almost damaged.

(Case 2)

After 300 days, 600 days, ... , since the delivery date of the optical fibers, the control unit 14 obtains the gain value which is set by the gain adjustment unit 40 on the measurement data acquired using the incident optical fibers 6a or the detection optical fibers 8a to be used in an actual measurement. Then storage unit 44 stores the gain value obtained with time. The graph shows that the gain value obtained with time suddenly increments from the 300th day to the 600th day after the delivery date. This is assumed due to excess strain placed on the incident optical fibers 6a or the detection optical fibers 8a.

The damage determination unit 46 determines that excess strain is placed on the incident optical fibers 6a or the detection optical fibers 8a and plural numbers of optical fibers are damaged at once, if the inclination of the gain value between the gain value after 300 days since the delivery date and the gain value after 600 days exceeds a predetermined value. The damage determination unit 46 displays a caution message on the display unit 36 that excess strain has been placed on the relevant incident optical fiber 6a or the detection optical fiber 8a.

As described above, in accordance with the present invention, an operator can estimate deterioration of optical fibers due to excess strain by tracking record of optical fibers' damage condition, thus can accurately acknowledge almost damaged optical fibers.

DESCRIPTION OF REFERENCE NUMERALS

2: object, 4: probe, 6: incident probe, 6a: incident optical fiber, 8: detection probe, 8a: detection optical fiber, 10: light source unit, 12: optical measurement unit, 14: control unit, 16: semiconductor laser, 18: optical module, 28: photoelectric transducer, 30: lock-in amplifier module, 32: A/D converter, 34: signal processing unit, 36: display unit, 38: storage unit, 39: operation unit, 40: gain adjustment unit, 42: gain comparison unit, 44: gain storage unit, 46: damage determination unit

The invention claimed is:

1. A biological optical measurement instrument comprising:
   a light source unit including an incident optical fiber that irradiates a near-infrared light;
   an optical measurement unit including a detection optical fiber that measures the passing light at a plurality of measurement points in an object to be examined;
   a signal processing unit configured to process the measurement data outputted from the optical measurement unit and thereby generating an image; and
   a display unit configured to display the measurement data, characterized in further comprising:

a gain adjustment unit configured to set a gain value on the measurement data detected by the optical measurement unit based on the light intensity of the passing light;

a gain storage unit configured to store a damage gain value set by the gain adjustment unit when a damaged incident optical unit or a damaged detection optical fiber is used;

a gain comparison unit configured to compare the gain value set by the gain adjustment unit and the damage gain value stored in the gain storage unit; and a damage determination unit configured to determine whether the incident optical fiber or the detection optical fiber is damaged or not based on the comparison result by the gain comparison unit, wherein the display unit displays the damage condition.

2. The biological optical measurement instrument according to claim 1, further comprising:

an inspection unit including a biological simulated sample for inspecting the incident optical fiber or the detection optical fiber, wherein the gain comparison unit compares the gain value acquired when the incident optical fiber or the detection optical fiber is inserted into the inspection unit with the damage gain value.

3. The biological optical measurement instrument according to claim 1, wherein the gain value in the gain adjustment unit and the damage gain value are set for uniformizing the light intensity.

4. The biological optical measurement instrument according to claim 1, wherein the gain storage unit stores the damage gain value using the incident optical fiber or the detection optical fiber of which a predetermined ratio of optical fibers are damaged.

5. The biological optical measurement instrument according to claim 1, wherein the damage determination unit determines whether the gain value is higher or lower than the damage gain value, and determines that the incident optical fiber or the detection optical fiber is damaged if the gain value is higher than the damage gain value.

6. The biological optical measurement instrument according to claim 1, wherein when the gain value is higher than the damage gain value, the display unit displays a warning message along with the positional information of the damaged incident optical fiber or the detection optical fiber.

7. The biological optical measurement instrument according to claim 1, wherein when the gain value is higher than the damage gain value, the display unit displays marks at the place having the high gain value.

8. The biological optical measurement instrument according to claim 7, wherein the display unit displays the number of the incident optical fiber or the detection optical fiber at which the marks are displayed in four places of the periphery thereof.

9. The biological optical measurement instrument according to claim 1, wherein the gain storage unit further stores a caution gain value which is set by the gain adjustment unit when an almost damaged incident optical fiber or an almost damaged detection optical fiber is used, and wherein the damage determination unit determines whether the gain value is higher or lower than the caution gain value, and determines that the incident optical fiber or the detection optical fiber is almost damaged if the gain value is higher than the caution gain value.

10. The biological optical measurement instrument according to claim 9, wherein the gain storage unit stores the gain value obtained with time, and wherein the damage determination unit calculates the day that the gain value surpasses the caution gain value by referring to transition of the gain value obtained with time.

11. The biological optical measurement instrument according to claim 1, wherein the gain storage unit stores the gain value obtained with time, and wherein the damage determination unit calculates the day that the gain value surpasses the damage gain value by referring to transition of the gain value obtained with time.

12. The biological optical measurement instrument according to claim 1, wherein the damage determination unit displays a caution message on the display unit if the inclination of the gain value obtained with time is greater than a predetermined value.

13. A method for determining damage of optical fibers comprising:

a step of setting a gain value on the measurement data detected by an optical measurement unit based on the light intensity of a passing light;

a step of storing a damage gain value to be set when a damaged incident optical fiber or a damaged detection optical fiber is used;

a step of comparing the gain value and the damage gain value; and a step of determining whether an incident optical fiber or a detection optical fiber is damaged or not by referring to the comparison result between the gain value and the damage gain value.

* * * * *